United States Patent [19]

Takemura et al.

[11] Patent Number: 5,411,935
[45] Date of Patent: May 2, 1995

[54] DIHYDROBENZOFURAN DERIVATIVES, THEIR PRODUCTION AND USE

[75] Inventors: Susumu Takemura, Takarazuka; Minoru Takano, Kameoka; Satoru Kizawa, Takarazuka; Kazuo Saito, Toyonaka, all of Japan

[73] Assignee: Sumitomo Chemical Co., Ltd., Osaka, Japan

[21] Appl. No.: 208,516

[22] Filed: Mar. 10, 1994

[30] Foreign Application Priority Data

Mar. 17, 1993 [JP] Japan .................. 5-057216

[51] Int. Cl.⁶ .................. A01N 43/54; C07D 239/46
[52] U.S. Cl. .................. 504/243; 544/310
[58] Field of Search .................. 544/310; 504/243

[56] References Cited

U.S. PATENT DOCUMENTS

| | | | |
|---|---|---|---|
| 4,859,229 | 8/1989 | Wenger et al. | 544/309 |
| 4,881,967 | 11/1989 | Semple | 544/48 |
| 5,169,431 | 12/1992 | Enomoto et al. | 544/310 |
| 5,280,010 | 1/1994 | Enomoto et al. | 544/310 |
| 5,332,717 | 7/1994 | Lüthy et al. | 544/310 |
| 5,346,881 | 9/1994 | Theodoridis | 544/310 |
| 5,354,730 | 10/1994 | Enomoto et al. | 544/310 |

FOREIGN PATENT DOCUMENTS

| | | |
|---|---|---|
| 255047 | 2/1988 | European Pat. Off. . |
| 271170 | 6/1988 | European Pat. Off. . |
| 476697 | 3/1992 | European Pat. Off. . |
| 517181 | 12/1992 | European Pat. Off. . |
| 561319 | 9/1993 | European Pat. Off. ............ 544/310 |
| WO14073 | 7/1993 | WIPO . |

*Primary Examiner*—Cecilia Tsang
*Attorney, Agent, or Firm*—Birch, Stewart, Kolasch & Birch

[57] ABSTRACT

There are disclosed novel dihydrobenzofuran derivatives of the formula:

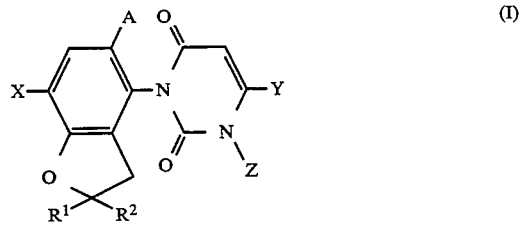

wherein A, X, Y, Z, $R^1$ and $R^2$ are each as defined in the description. Also disclosed are a herbicidal composition containing a herbicidally effective amount of the compound (I) as an active ingredient and a method for exterminating unfavorable weeds by applying a herbicidally effective amount of the compound (I) to an area where the unfavorable weeds grow or will grow.

20 Claims, No Drawings

DIHYDROBENZOFURAN DERIVATIVES, THEIR PRODUCTION AND USE

The present invention relates to novel dihydrobenzofuran derivatives and herbicidal compositions containing the same as active ingredients.

It is well known that certain kinds of substituted dihydrobenzofuran derivatives can be used as active ingredients of herbicides (see, e.g., U.S. Pat. No. 4,881,967).

These compounds, however, have insufficient herbicidal activity and poor selectivity between crop plants and weeds, and it cannot always be said that they are satisfactory for active ingredients of herbicides.

Under these circumstances, the present inventors have intensively studied various compounds. As a result, they have found that particular kinds of dihydrobenzofuran derivatives have excellent herbicidal activity and exhibit excellent selectivity between crop plants and weeds, thereby completing the present invention.

Thus, the present invention provides novel dihydrobenzofuran derivatives of the formula:

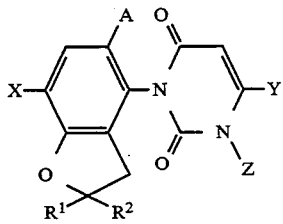

(I)

wherein A is hydrogen, fluorine or chlorine; X is hydrogen, fluorine, chlorine or bromine; Y is methyl optionally substituted with one or more halogen atoms; Z is methyl or amino; $R^1$ is $C_1$-$C_6$ alkyl; and $R^2$ is $C_1$-$C_6$ alkyl, $C_1$-$C_6$ haloalkyl, $C_1$-$C_6$ hydroxyl-alkyl, $C_1$-$C_6$ alkoxy($C_1$-$C_6$)alkyl, $C_1$-$C_6$ alkoxy($C_1$-$C_6$)alkoxy($C_1$-$C_6$)-alkyl, $C_1$-$C_7$ acyloxy($C_1$-$C_6$)alkyl, carboxyl, $C_1$-$C_6$ alkoxycarbonyl, $C_1$-$C_6$ haloalkoxycarbonyl, $C_3$-$C_6$ cycloalkoxycarbonyl, $C_2$-$C_6$ alkynyloxycarbonyl, aminocarbonyl, $C_1$-$C_6$ alkylaminocarbonyl or phenylaminocarbonyl having a phenyl group optionally substituted with $C_1$-$C_6$ alkyl, $C_1$-$C_6$ alkoxy, $C_1$-$C_6$ haloalkyl, $C_1$-$C_6$ haloalkoxy, halogen, nitro, cyano or $C_1$-$C_6$ alkylthio.

In the formula (I) as depicted above, examples of the acyl group are $C_1$-$C_6$ alkylcarbonyl, $C_1$-$C_6$ haloalkylcarbonyl, $C_3$-$C_6$ cycloalkylcarbonyl or benzoyl, and examples of the halogen atom are fluorine, chlorine and bromine.

The present invention also provides a herbicidal composition comprising a herbicidally effective amount of the compound (I) as an active ingredient and a method of exterminating unfavorable weeds by applying a herbicidally effective amount of the compound (I) to an area where the unfavorable weeds grow or will grow.

As to $R^1$, $C_1$-$C_3$ alkyl is preferred, and methyl is more preferred.

As to $R^2$, $C_1$-$C_3$ alkyl, $C_1$-$C_3$ haloalkyl, $C_1$-$C_3$ hydroxyalkyl, $C_1$-$C_3$ alkoxy-($C_1$-$C_3$)alkyl, $C_1$-$C_3$ alkoxy($C_1$-$C_3$)alkoxy($C_1$-$C_3$)alkyl, $C_1$-$C_7$ acyloxy($C_1$-$C_3$)alkyl, carboxyl, $C_1$-$C_6$ alkoxycarbonyl, $C_1$-$C_6$ haloalkoxycarbonyl, $C_3$-$C_6$ cycloalkoxycarbonyl or $C_2$-$C_4$ alkynyloxycarbonyl is preferred.

As to $R^2$, methyl, ethyl, fluoromethyl, chloromethyl, bromomethyl, fluoroethyl, chloroethyl, bromoethyl, hydroxymethyl, hydroxyethyl, methoxymethyl, ethoxymethyl, isopropyloxymethyl, methoxymethoxymethyl, ethoxymethoxymethyl, $C_1$-$C_7$ acyloxymethyl, $C_1$-$C_7$ acyloxyethyl, carboxyl, methoxycarbonyl, ethoxycarbonyl, n-propyloxycarbonyl, i-propyloxycarbonyl, n-butyloxycarbonyl, i-butyloxycarbonyl, t-butyloxycarbonyl, n-pentyloxycarbonyl, i-pentyloxycarbonyl, t-pentyloxycarbonyl, $C_1$-$C_3$ haloalkoxycarbonyl, cyclopentyloxycarbonyl or cyclohexyloxycarbonyl is more preferred.

As to X, fluorine, chlorine or bromine is preferred.

The following will describe some production processes for the compound (I).

Production Process (a)

The compound (I) wherein $R^2$ is $C_1$-$C_6$ alkyl can be produced by subjecting, to intramolecular cyclization, a compound of the formula:

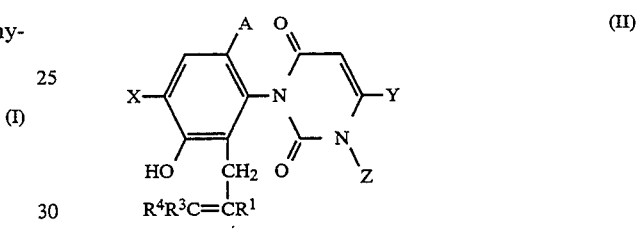

(II)

wherein $R^3$ and $R^4$ are the same or different and are hydrogen or $C_1$-$C_6$ alkyl with the proviso that the total number of carbon atoms in the $R^3$ and $R^4$ is not greater than 6, and A, X, Y, Z and $R^1$ are each as defined above.

The reaction is usually carried out without any solvent or in a solvent in the presence or absence of a catalyst at a temperature of 0° to 250° C., preferably 20° to 200° C., for a period of 0.5 to 24 hours. The catalyst is used in an amount of 0.01 to 0.5 moles to one mole of the compound (II).

Examples of the solvent are aliphatic hydrocarbons such as petroleum ether and hexane; aromatic hydrocarbons such as toluene and xylene; halogenated hydrocarbons such as chloroform, 1,2-dichloroethane, chlorobenzene and o-dichlorobenzene; ethers such as diethyl ether, diisopropyl ether, 1,4-dioxane, tetrahydrofuran and ethylene glycol dimethyl ether; ketones such as acetone, methyl isobutyl ketone and cyclohexanone; fatty acids such as formic acid and acetic acid; alcohols such as methanol, ethanol and ethylene glycol; nitro compounds such as nitroethane and nitrobenzene; nitriles such as acetonitrile and isobutyronitrile; acid amides such as formamide, N,N-dimethylformamide and acetamide; sulfur compounds such as dimethyl sulfoxide and sulforane; and water. These solvents may be used alone or in combination.

Examples of the catalyst are sulfonic acids such as p-toluenesulfonic acid and methanesulfonic acid; sulfonates such as pyridinium-p-toluenesulfonate; and mineral acids such as sulfuric acid and hydrochloric acid.

After completion of the reaction, the reaction mixture is subjected to ordinary post-treatment. For example, the reaction mixture is poured into water and the precipitated crystals are filtered by filtration, or alternatively the reaction mixture is extracted with an organic solvent and concentrated. If necessary, any purification such as chromatography, distillation or recrystallization, thus obtaining the desired compound.

The compound (II) can be produced by reacting a compound of the formula:

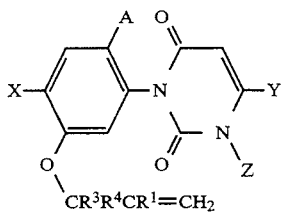

(III)

wherein A, X, Y, Z, $R^1$, $R^3$ and $R^4$ are each as defined above, without any solvent or in an solvent at a temperature of 20° to 300° C., preferably 100° to 250° C., for a period 0.5 to 48 hours.

Examples of the solvent are aliphatic hydrocarbons such as petroleum ether and hexane; aromatic hydrocarbons such as toluene, xylene and m-isobutylbenzene; halogenated hydrocarbons such as chloroform, 1,2-dichloroethane, chlorobenzene and o-dichlorobenzene; ethers such as diethyl ether, diisopropyl ether, 1,4-dioxane, tetra-hydrofuran and ethylene glycol dimethyl ether; ketones such as acetone, methyl isobutyl ketone and cyclohexanone; fatty acids such as formic acid and acetic acid; alcohols such as methanol, ethanol and ethylene glycol; esters such as ethyl acetate and diethyl carbon ate; nitro compounds such as nitroethane and nitrobenzene; nitriles such as acetonitrile and isobutyronitrile; tertiary amines such as pyridine, triethylamine, N,N-dimethylaniline, N,N-diethylaniline and N-methylmorpholine; acid amides such as formamide, N,N-dimethylformamide and acetamide; sulfur compounds such as dimethyl sulfoxide and sulforane; and water. These solvents may be used alone or in combination.

After completion of the reaction, the reaction mixture is subjected to ordinary post-treatment. For example, the reaction mixture is poured into water and the precipitated crystals are filtered by filtration, or alternatively the reaction mixture is extracted with an organic solvent and concentrated. If necessary, any purification such as chromatography, distillation or recrystallization, thus obtaining the desired compound.

The compound (III) can be produced according to the method as described in JP-A 63-41466 and EP-517181-A.

Production Process (b)

The compound (I) wherein $R^2$ is $C_1-C_6$ hydroxyalkyl can be produced by reacting the compound (II), which is the starting material of the production process (a), with an epoxidizing agent (the first step) and then subjecting the product to cyclization in the presence of a catalyst (the second step), if necessary, as depicted in the following scheme:

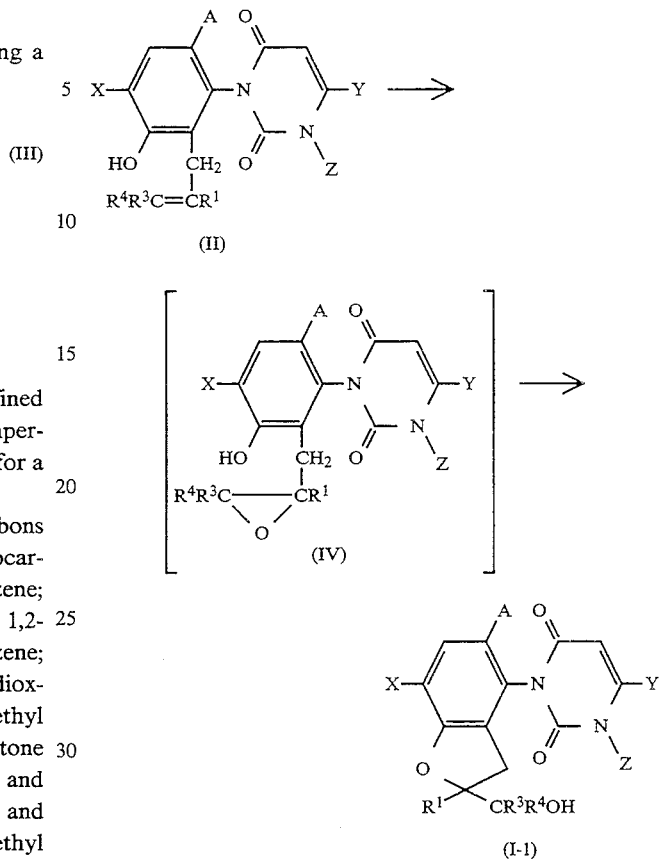

wherein A, X, Y, Z, $R^1$, $R^3$ and $R^4$ are each as defined above.

The first step is usually carded out in a solvent at a temperature of $-20°$ to 150° C., preferably 0° to 80° C., for a period of 0.5 to 24 hours. The epoxidizing agent is used in an amount of 1 to 5 moles to one mole of the compound (II).

Examples of the solvent which can be used in the first step are aliphatic hydrocarbons such as petroleum ether and hexane; fatty acids such as formic acid and acetic acid; and halogenated hydrocarbons such as methylene chloride, chloroform and 1,2-dichloroethane. Examples of the epoxidizing agent are peracids such as perbenzoic acid, m-chloroperbenzoic acid, peracetic acid and trifluoroperacetic acid.

After completion of the reaction, the reaction mixture is treated with a reducing agent such as aqueous sodium thiosulfate or aqueous sodium hydrogensulfite, and then subjected to ordinary post-treatments such as extraction with an organic solvent and concentration, after which any purification is employed, if necessary, such as chromatography or recrystallization, thus obtaining the compound (IV) or the desired compound (I-1 ) which is formed from the compound (IV) by direct cyclization.

The second step is usually carried out in a solvent in the presence or absence of a catalyst at a temperature of $-20°$ to 250° C., preferably 0° to 200° C., for a period of a moment to 24 hours. The catalyst is used in an amount of a catalytic amount to five moles to one mole of the compound (IV).

Examples of the solvent which can be used in the second step are aliphatic hydrocarbons such as petroleum ether and hexane; aromatic hydrocarbons such as toluene and xylene; halogenated hydrocarbons such as chloroform, 1,2-dichloroethane, chlorobenzene and o-dichlorobenzene; ethers such as diethyl ether, diisopropyl ether, 1,4-dioxane, tetrahydrofuran and ethylene glycol dimethyl ether; ketones such as acetone, methyl isobutyl ketone and cyclohexanone; fatty acids such as formic acid and acetic acid; alcohols such as methanol, ethanol and ethylene glycol; esters such as ethyl acetate and diethyl carbonate; nitro compounds such as nitroethane and nitrobenzene; nitriles such as acetonitrile and isobutyronitrile; tertiary amines such as pyridine, triethylamine, N,N-dimethylaniline, N,N-diethylaniline and N-methylmorpholine; acid amides such as formamide, N,N-dimethylformamide and acetamide; sulfur compounds such as dimethyl sulfoxide and sulforane; and water. These solvents may be used alone or in combination.

Depending upon the kind of solvent used, various catalysts may be used, examples of which are sulfonic acids such as p-toluenesulfonic acid and methanesulfonic acid; sulfonates such as pyridinium-p-toluenesulfonate; mineral acids such as sulfuric acid, hydrochloric acid and hydroperchloric acid; Lewis acids such as boron trifluoride diethyl etherate and zinc chloride; inorganic bases such as potassium carbonate, sodium hydroxide and potassium hydroxide; and metal hydrides such as sodium hydride and potassium hydride.

After completion of the reaction, the reaction mixture is subjected to ordinary post-treatment. For example, the reaction mixture is poured into water and the precipitated crystals are filtered by filtration, or alternatively the reaction mixture is extracted with an organic solvent and concentrated. If necessary, any purification such as chromatography, distillation or recrystallization, thus obtaining the desired compound.

Production Process (c)

The compound (I) wherein $R^2$ is $C_1$-$C_6$ alkoxy($C_1$-$C_6$)alkyl or $C_1$-$C_6$ alkoxy ($C_1$-$C_6$)alkoxy($C_1$-$C_6$)alkyl can be produced by reacting the compound (I-1), which is produced by the production process (b) as described above, with a compound of the formula:

$$R^5J \qquad\qquad\qquad\qquad (V)$$

wherein $R^5$ is $C_1$-$C_6$ alkyl or $C_1$-$C_6$ alkoxy($C_1$-$C_6$)alkyl, and J is halogen, methanesulfonyloxy or p-toluenesulfonyloxy.

The reaction is usually carded out in a solvent in the presence of a base at a temperature of $-20°$ C. to the reflux temperature of a solvent when used, for a period of a moment to 24 hours. The compound (V) and the base are used in the respective amounts of 1 to 10 moles to one mole of the compound (I-1).

Examples of the solvent are aliphatic hydrocarbons such as petroleum ether and hexane; aromatic hydrocarbons such as toluene and xylene; halogenated hydrocarbons such as chloroform, 1,2-dichloroethane, chlorobenzene and o-dichlorobenzene; ethers such as diethyl ether, diisopropyl ether, 1,4-dioxane, tetrahydrofuran and ethylene glycol dimethyl ether; ketones such as acetone, methyl isobutyl ketone and cyclohexanone; esters such as ethyl acetate and diethyl carbonate; nitro compounds such as nitroethane and nitrobenzene; nitriles such as acetonitrile and isobutyronitrile; tertiary amines such as pyridine, triethylamine, N,N-dimethylaniline, N,N-diethylaniline and N-methylmorpholine; acid amides such as formamide, N,N-dimethylformamide and acetamide; and sulfur compounds such as dimethyl sulfoxide and sulforane. These solvents may be used alone or in combination.

Examples of the base are inorganic bases such as potassium carbonate, sodium hydroxide and potassium hydroxide; metal hydrides such as sodium hydride and potassium hydride; and organic bases such as triethylamine, diisopropylethylamine, pyridine and 4-dimethylaminopyridine.

After completion of the reaction, the reaction mixture is subjected to ordinary post-treatment. For example, the reaction mixture is poured into water and the precipitated crystals are filtered by filtration, or alternatively the reaction mixture is extracted with an organic solvent and concentrated. If necessary, any purification such as chromatography, distillation or recrystallization, thus obtaining the desired compound.

Production Process (d)

The compound (I) wherein $R^2$ is $C_1$-$C_7$ acyloxyalkyl can be produced by reacting the compound (I-1), which is produced by the production process (b), with a compound of the formula:

$$R^6G \qquad\qquad\qquad\qquad (VI)$$

wherein $R^6$ is $C_1$-$C_7$ acyl and G is chlorine or bromine, or a compound of the formula:

$$(R^6)_2O \qquad\qquad\qquad\qquad (VII)$$

wherein $R^6$ is as defined above.

The reaction is usually carried out without any solvent or in a solvent in the presence of a base at a temperature of $-20°$ to $200°$ C., preferably $0°$ C. to the reflux temperature of a solvent when used, or preferably $0°$ to $100°$ C. when no solvent is used, for a period of a moment to 24 hours. The compound (VI) or (VII) and the base are used in the respective amounts of one mole to in large excess to one mole of the compound (I-1).

Examples of the solvent are aliphatic hydrocarbons such as petroleum ether and hexane; aromatic hydrocarbons such as toluene and xylene; halogenated hydrocarbons such as chloroform, 1,2-dichloroethane, chlorobenzene and o-dichlorobenzene; ethers such as diethyl ether, diisopropyl ether, 1,4-dioxane, tetrahydrofuran and ethylene glycol dimethyl ether; ketones such as acetone, methyl isobutyl ketone and cyclohexanone; esters such as ethyl acetate and diethyl carbonate; nitro compounds such as nitroethane and nitrobenzene; nitriles such as acetonitrile and isobutyronitrile; tertiary amines such as pyridine, triethylamine, N,N-dimethylaniline, N,N-diethylaniline and N-methylmorpholine; acid amides such as formamide, N,N-dimethylformamide and acetamide; and sulfur compounds such as dimethyl sulfoxide and sulforane. These solvents may be used alone or in combination.

Examples of the base are inorganic bases such as potassium carbonate, sodium hydroxide and potassium hydroxide; metal hydrides such as sodium hydride and potassium hydride; and organic bases such as triethylamine, diisopropylethylamine, pyridine and 4-dimethylaminopyridine.

After completion of the reaction, the reaction mixture is subjected to ordinary post-treatment. For example, the reaction mixture is concentrated; the reaction mixture is poured into water and the precipitated crystals are filtered by filtration; or the reaction mixture is extracted with an organic solvent and concentrated. If necessary, any purification such as chromatography or recrystallization, thus obtaining the desired compound.

The compound (I) wherein $R^2$ is acyloxyalkyl can be produced by reacting the compound (I-1), which is produced by the production process (b), with a compound of the formula:

$$R^6\text{—OH} \qquad (\text{VII-2})$$

wherein $R^6$ is as defined above.

The reaction is usually carried out without any solvent or in a solvent in the presence of an acid or a condensing agent at a temperature of 0° to 200° C., preferably 10° C. to the reflux temperature of a solvent when used, or preferably 10° to 100° C. when no solvent is used, for a period of a moment to 24 hours. The compound (VII-2) is used in an amount of one mole to in large excess to one mole of the compound (I-1). The acid is used in a catalytic amount or up to the amount of one mole to one mole of the compound (I-1). The condensing agent is used in an amount of 1 to 5 moles to one mole of the compound (I-1).

Examples of the solvent are aliphatic hydrocarbons such as petroleum ether and hexane; aromatic hydrocarbons such as toluene and xylene; halogenated hydrocarbons such as chloroform, 1,2-dichloroethane, chlorobenzene and o-dichlorobenzene; ethers such as diethyl ether, diisopropyl ether, 1,4-dioxane, tetrahydrofuran and ethylene glycol dimethyl ether; ketones such as acetone, methyl isobutyl ketone and cyclohexanone; esters such as ethyl acetate and diethyl carbonate; nitro compounds such as nitroethane and nitrobenzene; nitriles such as acetonitrile and isobutyronitrile; tertiary amines such as pyridine, triethylamine, N,N-dimethylaniline, N,N-diethylaniline and N-methylmorpholine; acid amides such as formamide, N,N-dimethylformamide and acetamide; and sulfur compounds such as dimethyl sulfoxide and sulforane. These solvents may be used alone or in combination.

Examples of the acid are sulfonic acids such as p-toluenesulfonic acid and methanesulfonic acid; sulfonates such as pyridinium-p-toluenesulfonate; and mineral acids such as sulfuric acid and hydrochloric acid.

Examples of the condensing agent are N,N'-disubstituted carbodiimide such as N,N'-dicyclohexylcarbodiimide; 2,4,6-trimethylbenzenesulfonyl chloride and N,N$\alpha$-carbonyldiimidazole.

After completion of the reaction, the reaction mixture is subjected to ordinary post-treatment. For example, the reaction mixture is concentrated; the reaction mixture is poured into water and the precipitated crystals are filtered by filtration; or the reaction mixture is extracted with an organic solvent and concentrated. If necessary, any purification such as chromatography or recrystallization, thus obtaining the desired compound.

Production Process (e)

The compound (I) wherein $R^2$ is carboxyl can be produced by oxidizing the compound (I-1) wherein $R^3$ and $R^4$ are both hydrogen with an oxidizing agent.

The reaction is usually carded out in a solvent at a temperature of $-80°$ to 100° C., preferably 0° to 50° C., for a period of 0.5 to 12 hours. The oxidizing agent is used in an amount of one mole to in large excess to one mole of the compound (I-1).

Examples of the oxidizing agent are permanganates such as potassium permanganate; chromic acids such as chromium trioxide/sulfuric acid, potassium dichromate and pyridinium dichromate; and oxygen gas.

Depending upon the kind of oxidizing agent used, various solvents may be used, examples of which are aliphatic hydrocarbons such as petroleum ether and hexane; aromatic hydrocarbons such as toluene and xylene; halogenated hydrocarbons such as chloroform, 1,2-dichloroethane, chlorobenzene and o-dichlorobenzene; ketones such as acetone, methyl isobutyl ketone and cyclohexanone; fatty acids such as formic acid and acetic acid; esters such as ethyl acetate and diethyl carbonate; acid amides such as formamide, N,N-dimethylformamide and acetamide; sulfur compounds such as dimethyl sulfoxide and sulforane; and water. These solvents may be used alone or in combination.

After completion of the reaction, the reaction mixture is subjected to ordinary post-treatment. For example, the reaction mixture is poured into water and the precipitated crystals are filtered by filtration, or alternatively the reaction mixture is extracted with an organic solvent and concentrated. If necessary, any purification such as chromatography, distillation or recrystallization, thus obtaining the desired compound.

Production Process (f)

The compound (I) wherein $R^2$ is $C_1$–$C_6$ alkoxycarbonyl, $C_1$–$C_6$ haloalkoxycarbonyl, $C_3$–$C_6$ cycloalkoxycarbonyl or $C_2$–$C_6$ alkynyloxycarbonyl can be produced by reacting the compound (I) wherein $R^2$ is carboxyl, which is produced by the production process (e), with a compound of the formula:

$$R^7\text{—OH} \qquad (\text{VII})$$

wherein $R^7$ is $C_1$–$C_6$ alkyl, $C_1$–$C_6$ haloalkyl, $C_3$–$C_6$ cycloalkyl or $C_2C_6$ alkynyl.

The reaction is usually carried out without any solvent or in a solvent in the presence of an acid at a temperature of 20° to 200° C., preferably 60° to 120° C., for a period of 0.5 to 24 hours. The compound (VIII) and the acid are used in amounts of one mole to in large excess and a catalytic amount to 0.5 moles, respectively, to one mole of the compound (I) wherein $R^2$ is carboxyl.

Examples of the acid are mineral acids such as sulfuric acid and hydrochloric acid; and sulfonic acids such as p-toluenesulfonic acid.

Examples of the solvent are aliphatic hydrocarbons such as petroleum ether and hexane; aromatic hydrocarbons such as toluene and xylene; halogenated hydrocarbons such as chloroform, 1,2-dichloroethane, chlorobenzene and o-dichlorobenzene; ethers such as diethyl ether, diisopropyl ether, 1,4-dioxane, tetrahydrofuran and ethylene glycol dimethyl ether; acid amides such as formamide, N,N-dimethylformamide and acetamide; and sulfur compounds such as dimethyl sulfoxide and sulforane. These solvents may be used alone or in combination.

After completion of the reaction, the reaction mixture is subjected to ordinary post-treatment. For example, the reaction mixture is poured into water and the precipitated crystals are filtered by filtration, or alternatively the reaction mixture is extracted with an organic solvent and concentrated. If necessary, any purification such as chromatography, distillation or recrystallization, thus obtaining the desired compound.

The compound (I) wherein $R^2$ is alkoxycarbonyl, haloalkoxycarbonyl, cycloalkoxycarbonyl or alkynyloxycarbonyl can be produced by converting the compound (I) wherein $R^2$ is carboxyl, which is produced by the production process (e), into its activated reactive derivative according to a chemically acceptable method and then reacting this derivative with the compound (VIII).

For the activation, various methods can be used, such as those using phosgene, oxalyl chloride, thionyl chloride, phosphorous oxychloride, N,N'-carbonyl diimidazole, N,N'-dicyclohexylcarbodiimide or 2,4,6-trimethylbenzenesulfonyl chloride.

The reaction of the reactive derivative with the compound (VIII) is usually carried out in a solvent in the presence or absence of a base at a temperature of $-20°$ to $100°$ C. for a period of a moment to 24 hours. The compound (VIII) is used in an amount of one mole to in large excess to one mole of the compound (I) wherein $R^2$ is carboxyl. The base is used in an amount of 1 to 5 moles to one mole of the compound (I) wherein $R^2$ is carboxyl.

Examples of the solvent are aliphatic hydrocarbons such as petroleum ether and hexane; aromatic hydrocarbons such as toluene and xylene; halogenated hydrocarbons such as chloroform, 1,2-dichloroethane, chlorobenzene and o-dichlorobenzene; ethers such as diethyl ether, diisopropyl ether, 1,4-dioxane, tetrahydrofuran and ethylene glycol dimethyl ether; ketones such as acetone, methyl isobutyl ketone and cyclohexanone; nitro compounds such as nitroethane and nitrobenzene; nitriles such as acetonitrile and isobutyronitrile; tertiary amines such as pyridine, triethylamine, N,N-dimethylaniline, N,N-diethylaniline and N-methylmorpholine; acid amides such as formamide, N,N-dimethylformamide and acetamide; and sulfur compounds such as dimethyl sulfoxide and sulforane. These solvents may be used alone or in combination.

Examples of the base are inorganic bases such as potassium carbonate, sodium hydroxide and potassium hydroxide; and tertiary amines such as pyridine and triethylamine.

After completion of the reaction, the reaction mixture is subjected to ordinary post-treatment. For example, the reaction mixture is poured into water and the precipitated crystals are filtered by filtration, or alternatively the reaction mixture is extracted with an organic solvent and concentrated. If necessary, any purification such as chromatography, distillation or recrystallization, thus obtaining the desired compound.

Production Process (g)

The compound (I) wherein $R^2$ is aminocarbonyl, $C_1$-$C_6$ alkylaminocarbonyl or phenylaminocarbonyl having a phenyl group optionally substituted with $C_1$-$C_6$ alkyl, $C_1$-$C_6$ alkoxy, $C_1$-$C_6$ haloalkyl, $C_1$-$C_6$ haloalkoxy, halogen, nitro, cyano or $C_1$-$C_6$ thioalkyl can be produced by convening the compound (I) wherein $R^2$ is carboxyl, which is produced by the production process (e), into its reactive derivative according to the production process (f) as described above and then reacting this derivative with a compound of the formula:

$$R^8R^9NH \qquad (IX)$$

wherein $R^8$ and $R^9$ are the same or different and are independently hydrogen, $C_1$-$C_6$ alkyl or phenyl optionally substituted with $C_1$-$C_6$ alkyl, $C_1$-$C_6$ alkoxy, $C_1$-$C_6$ haloalkyl, $C_1$-$C_6$ haloalkoxy, halogen, nitro, cyano or $C_1$-$C_6$ thioalkyl.

The reaction is usually carried out in a solvent at a temperature of $0°$ to $100°$ C., preferably $5°$ to $80°$ C., for a period of a moment to 24 hours. The compound (IX) is used in an amount of one mole to in large excess to one mole of the compound (I) wherein $R^2$ is carboxyl.

Examples of the solvent are aliphatic hydrocarbons such as petroleum ether and hexane; aromatic hydrocarbons such as toluene and xylene; halogenated hydrocarbons such as chloroform, 1,2-dichloroethane, chlorobenzene and o-dichlorobenzene; ethers such as diethyl ether, diisopropyl ether, 1,4-dioxane, tetrahydrofuran and ethylene glycol dimethyl ether; ketones such as acetone, methyl isobutyl ketone and cyclohexanone; esters such as ethyl acetate and diethyl carbonate; nitro compounds such as nitroethane and nitrobenzene; nitriles such as acetonitrile and isobutyronitrile; tertiary amines such as pyridine, triethylamine, N,N-dimethylaniline, N,N-diethylaniline and N-methylmorpholine; acid amides such as formamide, N,N-dimethylformamide and acetamide; and sulfur compounds such as dimethyl sulfoxide and sulforane. These solvents may be used alone or in combination.

After completion of the reaction, the reaction mixture is subjected to ordinary post-treatment. For example, the reaction mixture is poured into water and the precipitated crystals are filtered by filtration, or alternatively the reaction mixture is extracted with an organic solvent and concentrated. If necessary, any purification such as chromatography, distillation or recrystallization, thus obtaining the desired compound.

Production Process (h)

The compound (I) wherein $R^2$ is $C_1$-$C_6$ haloalkyl can be produced by halogenating the compound (I-1), which is produced by the production process (b), with a halogenating agent.

The reaction is usually carded out without any solvent or in a solvent at a temperature of $-20°$ to $200°$ C., preferably $0°$ to $150°$ C., for a period of 0.5 to 24 hour. The halogenating agent is used in an amount of 1 to 10 moles to one mole of the compound (I-1).

Examples of the solvent are halogenated hydrocarbons such as dichloromethane, and chloroform and; aromatic hydrocarbons such as toluene and xylene; and ethers such as diethyl ether and tetrahydrofuran.

Examples of the halogenating agent are fluorinating agents such as diethylaminosulfur trifluoride; chlorinating agents such as carbon tetrachloride/triphenylphosphine; and brominating agents such as carbon tetrabromide/triphenylphosphine.

After completion of the reaction, the reaction mixture is subjected to ordinary post-treatment. For example, the reaction mixture is poured into water and the precipitated crystals are filtered by filtration, or alternatively the reaction mixture is extracted with an organic solvent and concentrated. If necessary, any purification such as chromatography, distillation or recrystallization, thus obtaining the desired compound.

According to any one of the above production processes (a) to (h), various compounds of the formula (I) are obtained as show in Table 1 where the symbols (n) and (c) denote normal chain alkyl and cycloalkyl groups, respectively.

TABLE 1

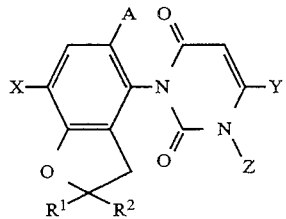

(I)

| Compound No. | A | X | Y | Z | R¹ | R² |
|---|---|---|---|---|---|---|
| (1) | F | Cl | CF$_3$ | CH$_3$ | CH$_3$ | CH$_3$ |
| (2) | F | Cl | CF$_3$ | CH$_3$ | CH$_3$ | C$_2$H$_5$ |
| (3) | F | Cl | CF$_3$ | CH$_3$ | CH$_3$ | C$_3$H$_7$(n) |
| (4) | F | Cl | CF$_3$ | CH$_3$ | CH$_3$ | CH$_2$OH |
| (5) | F | Cl | CF$_3$ | CH$_3$ | CH$_3$ | CH$_2$F |
| (6) | F | Cl | CF$_3$ | CH$_3$ | CH$_3$ | CH$_2$Cl |
| (7) | F | Cl | CF$_3$ | CH$_3$ | CH$_3$ | CH$_2$Br |
| (8) | F | Cl | CF$_3$ | CH$_3$ | CH$_3$ | CH$_2$I |
| (9) | F | Cl | CF$_3$ | CH$_3$ | CH$_3$ | CH$_2$OCH$_3$ |
| (10) | F | Cl | CF$_3$ | CH$_3$ | CH$_3$ | CH$_2$OCH$_2$OCH$_3$ |
| (11) | F | Cl | CF$_3$ | CH$_3$ | CH$_3$ | CH$_2$OCOCH$_3$ |
| (12) | F | Cl | CF$_3$ | CH$_3$ | CH$_3$ | CH$_2$OCOCH$_2$Cl |
| (13) | F | Cl | CF$_3$ | CH$_3$ | CH$_3$ | CH$_2$OCOCHCl$_2$ |
| (14) | F | Cl | CF$_3$ | CH$_3$ | CH$_3$ | CH$_2$OCOCCl$_3$ |
| (15) | F | Cl | CF$_3$ | CH$_3$ | CH$_3$ | CH$_2$OCOC$_2$H$_5$ |
| (16) | F | Cl | CF$_3$ | CH$_3$ | CH$_3$ | CH$_2$OCOC$_3$H$_7$(n) |
| (17) | F | Cl | CF$_3$ | CH$_3$ | CH$_3$ | CH$_2$OCOCH(CH$_3$)$_2$ |
| (18) | F | Cl | CF$_3$ | CH$_3$ | CH$_3$ | CH$_2$OCOC$_4$H$_9$(n) |
| (19) | F | Cl | CF$_3$ | CH$_3$ | CH$_3$ | CH$_2$OCOCH$_2$CH(CH$_3$)$_2$ |
| (20) | F | Cl | CF$_3$ | CH$_3$ | CH$_3$ | CH$_2$OCOC(CH$_3$)$_3$ |
| (21) | F | Cl | CF$_3$ | CH$_3$ | CH$_3$ | CH$_2$OCOC$_5$H$_9$(c) |
| (22) | F | Cl | CF$_3$ | CH$_3$ | CH$_3$ | CH$_2$OCOC$_6$H$_{11}$(c) |
| (23) | F | Cl | CF$_3$ | CH$_3$ | CH$_3$ | COOH |
| (24) | F | Cl | CF$_3$ | CH$_3$ | CH$_3$ | COOCH$_3$ |
| (25) | F | Cl | CF$_3$ | CH$_3$ | CH$_3$ | COOC$_2$H$_5$ |
| (26) | F | Cl | CF$_3$ | CH$_3$ | CH$_3$ | COOCH$_2$CH$_2$F |
| (27) | F | Cl | CF$_3$ | CH$_3$ | CH$_3$ | COOCH$_2$CH$_2$Cl |
| (28) | F | Cl | CF$_3$ | CH$_3$ | CH$_3$ | COOC$_3$H$_7$(n) |
| (29) | F | Cl | CF$_3$ | CH$_3$ | CH$_3$ | COOCH(CH$_3$)$_2$ |
| (30) | F | Cl | CF$_3$ | CH$_3$ | CH$_3$ | COOCH$_2$CH$_2$CH$_2$Cl |
| (31) | F | Cl | CF$_3$ | CH$_3$ | CH$_3$ | COOCH(CH$_3$)CH$_2$Cl |
| (32) | F | Cl | CF$_3$ | CH$_3$ | CH$_3$ | COOC$_4$H$_9$(n) |
| (33) | F | Cl | CF$_3$ | CH$_3$ | CH$_3$ | COOCH$_2$CH(CH$_3$)$_2$ |
| (34) | F | Cl | CF$_3$ | CH$_3$ | CH$_3$ | COOC(CH$_3$)$_3$ |
| (35) | F | Cl | CF$_3$ | CH$_3$ | CH$_3$ | COOC$_5$H$_9$(c) |
| (36) | F | Cl | CF$_3$ | CH$_3$ | CH$_3$ | COOC$_5$H$_{11}$(n) |
| (37) | F | Cl | CF$_3$ | CH$_3$ | CH$_3$ | COOC$_6$H$_{13}$(n) |
| (38) | F | Cl | CF$_3$ | CH$_3$ | CH$_3$ | COOCH$_2$C≡CH |
| (39) | F | Cl | CF$_3$ | CH$_3$ | CH$_3$ | CH$_2$OCOC$_6$H$_5$ |
| (40) | F | Br | CF$_3$ | CH$_3$ | CH$_3$ | CH$_3$ |
| (41) | F | Cl | CF$_3$ | NH$_2$ | CH$_3$ | CH$_3$ |
| (42) | F | Cl | CF$_3$ | CH$_3$ | CH$_3$ | CONH$_2$ |
| (43) | F | Cl | CF$_3$ | CH$_3$ | CH$_3$ | CON(CH$_3$)$_2$ |
| (44) | H | Cl | CF$_3$ | CH$_3$ | CH$_3$ | CH$_3$ |
| (45) | H | Cl | CF$_3$ | CH$_3$ | CH$_3$ | C$_2$H$_5$ |
| (46) | H | Cl | CF$_3$ | CH$_3$ | CH$_3$ | CH$_2$F |
| (47) | H | Cl | CF$_3$ | CH$_3$ | CH$_3$ | CH$_2$Cl |
| (48) | H | Cl | CF$_3$ | CH$_3$ | CH$_3$ | CH$_2$Br |
| (49) | H | Cl | CF$_3$ | CH$_3$ | CH$_3$ | CH$_2$OH |
| (50) | H | Cl | CF$_3$ | CH$_3$ | CH$_3$ | CH$_2$OCH$_3$ |
| (51) | H | Cl | CF$_3$ | CH$_3$ | CH$_3$ | CH$_2$OC$_2$H$_5$ |
| (52) | H | Cl | CF$_3$ | CH$_3$ | CH$_3$ | CH$_2$OCH(CH$_3$)$_2$ |
| (53) | H | Cl | CF$_3$ | CH$_3$ | CH$_3$ | CH$_2$OCH$_2$OCH$_3$ |
| (54) | H | Cl | CF$_3$ | CH$_3$ | CH$_3$ | CH$_2$OCH$_2$OC$_2$H$_5$ |
| (55) | H | Cl | CF$_3$ | CH$_3$ | CH$_3$ | CH$_2$OCH$_2$CH$_2$OCH$_3$ |
| (56) | H | Cl | CF$_3$ | CH$_3$ | CH$_3$ | CH$_2$OCOCH$_3$ |
| (57) | H | Cl | CF$_3$ | CH$_3$ | CH$_3$ | CH$_2$OCOC$_2$H$_5$ |
| (58) | H | Cl | CF$_3$ | CH$_3$ | CH$_3$ | CH$_2$OCOCH(CH$_3$)$_2$ |
| (59) | H | Cl | CF$_3$ | CH$_3$ | CH$_3$ | CH$_2$OCOC$_4$H$_9$(n) |
| (60) | H | Cl | CF$_3$ | CH$_3$ | CH$_3$ | CH$_2$OCOCH$_2$Cl |
| (61) | H | Cl | CF$_3$ | CH$_3$ | CH$_3$ | CH$_2$OCOCHCl$_2$ |
| (62) | H | Cl | CF$_3$ | CH$_3$ | CH$_3$ | CH$_2$OCOCCl$_3$ |
| (63) | H | Cl | CF$_3$ | CH$_3$ | CH$_3$ | CH$_2$OCOCF$_3$ |
| (64) | H | Cl | CF$_3$ | CH$_3$ | CH$_3$ | CH$_2$OCOCH$_2$CH(CH$_3$)$_2$ |
| (65) | H | Cl | CF$_3$ | CH$_3$ | CH$_3$ | CH$_2$OCOC(CH$_3$)$_3$ |
| (66) | H | Cl | CF$_3$ | CH$_3$ | CH$_3$ | CH$_2$OCOC$_6$H$_5$ |
| (67) | H | Cl | CF$_3$ | CH$_3$ | CH$_3$ | CH$_2$OCOC$_6$H$_{11}$(c) |

TABLE 1-continued

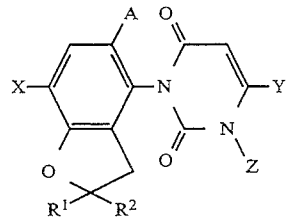

(I)

| Compound No. | A | X | Y | Z | R¹ | R² |
|---|---|---|---|---|---|---|
| (68) | H | Cl | CF$_3$ | CH$_3$ | CH$_3$ | CH$_2$OCOCF$_2$H |
| (69) | H | Cl | CF$_3$ | CH$_3$ | CH$_3$ | COOH |
| (70) | H | Cl | CF$_3$ | CH$_3$ | CH$_3$ | COOCH$_3$ |
| (71) | H | Cl | CF$_3$ | CH$_3$ | CH$_3$ | COOC$_2$H$_5$ |
| (72) | H | Cl | CF$_3$ | CH$_3$ | CH$_3$ | COOC$_3$H$_7$(n) |
| (73) | H | Cl | CF$_3$ | CH$_3$ | CH$_3$ | COOC$_4$H$_9$(n) |
| (74) | H | Cl | CF$_3$ | CH$_3$ | CH$_3$ | COOC$_5$H$_{11}$(n) |
| (75) | H | Cl | CF$_3$ | CH$_3$ | CH$_3$ | COOCH(CH$_3$)$_2$ |
| (76) | H | Cl | CF$_3$ | CH$_3$ | CH$_3$ | COOC(CH$_3$)$_3$ |
| (77) | H | Cl | CF$_3$ | CH$_3$ | CH$_3$ | COOCH$_2$CH$_2$F |
| (78) | H | Cl | CF$_3$ | CH$_3$ | CH$_3$ | COOCH$_2$CH$_2$Cl |
| (79) | H | Cl | CF$_3$ | CH$_3$ | CH$_3$ | COOCH(CH$_2$F)$_2$ |
| (80) | H | Cl | CF$_3$ | CH$_3$ | CH$_3$ | COOC$_6$H$_{11}$(c) |
| (81) | F | Cl | CF$_2$Cl | CH$_3$ | CH$_3$ | CH$_3$ |
| (82) | F | Cl | CF$_2$Cl | CH$_3$ | CH$_3$ | CH$_2$Br |
| (83) | F | Cl | CF$_2$Cl | CH$_3$ | CH$_3$ | CH$_2$OH |
| (84) | F | Cl | CF$_2$Cl | CH$_3$ | CH$_3$ | CH$_2$OCH$_3$ |
| (85) | F | Cl | CF$_2$Cl | CH$_3$ | CH$_3$ | CH$_2$OCH$_2$OCH$_3$ |
| (86) | F | Cl | CF$_2$Cl | CH$_3$ | CH$_3$ | CH$_2$OCOCH$_3$ |
| (87) | F | Cl | CF$_2$Cl | CH$_3$ | CH$_3$ | COOH |
| (88) | F | Cl | CF$_2$Cl | CH$_3$ | CH$_3$ | COOCH$_3$ |
| (89) | H | Cl | CF$_2$Cl | CH$_3$ | CH$_3$ | CH$_3$ |
| (90) | H | Cl | CF$_2$Cl | CH$_3$ | CH$_3$ | CH$_2$Br |
| (91) | H | Cl | CF$_2$Cl | CH$_3$ | CH$_3$ | CH$_2$OH |
| (92) | H | Cl | CF$_2$Cl | CH$_3$ | CH$_3$ | CH$_2$OCH$_3$ |
| (93) | H | Cl | CF$_2$Cl | CH$_3$ | CH$_3$ | CH$_2$OCH$_2$OCH$_3$ |
| (94) | H | Cl | CF$_2$Cl | CH$_3$ | CH$_3$ | CH$_2$OCOCH$_3$ |
| (95) | H | Cl | CF$_2$Cl | CH$_3$ | CH$_3$ | COOH |
| (96) | H | Cl | CF$_2$Cl | CH$_3$ | CH$_3$ | COOCH$_3$ |

The compounds (I) of the present invention have excellent herbicidal activity and some of them exhibit excellent selectivity between crop plants and weeds. That is, the compounds (I) of the present invention have herbicidal activity against various unfavorable weeds as recited below under the foliar treatment or soil treatment on upland fields.

Polygonaceae:
wild buckwheat (*Polygonum convolvulus*), pale smartweed (*Polygonum lapathifolium*), Pennsylvania smartweed (*Polygonum pensylvanicum*), ladysthumb (*Polygonum persicaria*), curly dock (*Rumex crispus*), broadleaf dock (*Rumex obtusifolius*)

Portulacaceae:
common purslane (*Portulaca oleracea*)

Caryophyllaceae:
common chickweed (*Stellaria media*)

Chenopodiaceae:
common lambsquarters (*Chenopodium album*), kochia (*Kochia scoparia*)

Amaranthaceae:
redroot pigweed (*Amaranthus retroflexus*), smooth pigweed (*Amaranthus hybridus*)

Crusiferae:
wild radish (*Raphanus raphanistrum*), wild mustard (*Brassica kaber*), shepherdspurse (*Capsella bursa-pastoris*)

Leguminosae:

hemp sesbania (*Sesbania exaltata*), sicklepod (*Cassia obtusifolia*), Florida beggarweed (*Desmodium tortuosum*), white clover (*Trifolium repens*)

Malvaceae:
velvetleaf (*Abutilon theophrasti*), prickly sida (*Sida spinosa*)

Violaceae:
field pansy (*Viola arvensis*), wild pansy (*Viola tricolor*)

Rubiaceae:
catchweed bedstraw (cleavers) (*Galium aparine*)

Convolvulaceae:
ivyleaf morningglory (*Ipomoea hederacea*), tall morningglory (*Ipomoea purpurea*), entireleaf morningglory (*Ipomoea hederacea* var. integriuscula), pitted morningglory (*Ipomoea lacunosa*), field bindweed (*Convolvulus arvensis*)

Labiatae:
red deadnettle (*Lamium purpureum*), henbit (*Lamium amplexicaule*)

Solanaceae:
jimsonweed (*Datura stramonium*), black nightshade (*Solanum nigrum*)

Scrophulariaceae:
birdseye speedwell (*Veronica persica*),ivyleaf speedwell (*Veronica hederaefolia*)

Compositae:
common cocklebur (Xanthium pensylvanicum), common sunflower (*Helianthus annuus*), scentless chamomile (*Matricaria inodora*), corn marigold (*Chrysanthemum segetum*), pineappleweed (*Matricaria matricarioides*), common ragweed (*Ambrosia artemisiifolia*), giant ragweed (*Ambrosia trifida*), horseweed (*Erigeron canadensis*)

Boraginaceae:
field forget-me-not (*Myosotis arvensis*)

Asclepiadaceae:
common milkweed (*Asclepias syriaca*)

Euphorbiaceae:
sun spurge (*Euphorbia helioscopia*), spotted spurge (*Euphorbia maculata*)

Gramineae:
barnyardgrass (*Echinochloa crus-galli*), green foxtail (*Setaria viridis*), giant foxtail (*Setaria faberi*), large crabgrass (*Digitaria sanguinalis*), goosegrass (*Eleusine indica*), annual bluegrass (*Poa annua*), blackgrass (*Alopecurus myosuroides*), wild oat (*Avena fatua*), Johnsongrass (*Sorghum halepense*), quackgrass (*Agropyron repens*), downy brome (*Bromus tectorum*), bermudagrass (*Cynodon dactylon*), fall panicum (*Panicum dichotomiflorum*), Texas panicum (*Panicum texanum*), shattercane (*Sorghum vulgare*)

Commelinaceae:
common dayflower (*Commelina communis*)

Equisetaceae:
field horsetail (*Equisetum arvense*)

Cyperaceae:
rice flatsedge (*Cyperus iria*), purple nutsedge (*Cyperus rotundus*), yellow nutsedge (*Cyperus esculentus*)

Further, some of the compounds (I) of the present invention have no problematic phytotoxicity on main crops such as corn (*Zea mays*), wheat (*Triticum aestivum*), barley (*Hordeum vulgare*), rice (*Oryza sativa*), sorghum (*Sorghum bicolor*), soybean (*Glycine max*), cotton (*Gossypium spp.*), sugar beet (*Beta vulgaris*), peanut (*Arachis hypogaea*), sunflower (Helianthus annuus) and canola (*Brassica napus*); and garden crops such as flowers and ornamental plants, and vegetables. In particular, the compounds (I) wherein $R^2$ is carboxyl or alkoxycarbonyl have excellent selectivity between soybean and weeds such as tall morningglory, barnyardgrass and Johnsongrass under the soil treatment on upland fields.

In addition, the compounds (I) of the present invention can be very effective against unfavorable weeds in the no-till cultivation. Further, some of them exhibit no problematic phytotoxicity on crop plants such as soybean, corn and wheat.

The compounds (I) of the present invention also have herbicidal activity against various unfavorable weeds as recited below under the flooding treatment on paddy rice fields.

Gramineae:
barnyardgrass (*Echinochloa oryzicola*)

Scrophulariaceae:
common falsepimpernel (*Lindernia procurebens*)

Lythraceae:
*Rotala indica, Ammannia multiflora*

Elatinaceae:
*Elatine triandra*

Cyperaceae:
smallflower umbellaplant (*Cyperus difformis*), hardstem bulrush (*Scirpus juncoides*), needle spikerush (*Eleocharis acicularis*), *Cyperus serotinus, Eleocharis kuroguwai*

Pontederiaceae:
*Monochoria vaginalis*

Alismataceae:
*Sagittaria pygmaea, Sagittaria trifolia, Alisma canaliculatum*

Potamogetonaceae:
roundleaf pondweed (*Potamogeton distinctus*)

Umbelliferae:
*Oenanthe javanica*

Further, some of the compounds (I) of the present invention also have no problematic phytotoxicity on transplanted paddy rice or directly-sown paddy rice.

Further, the compounds (I) of the present invention can be very effective against various unfavorable weeds in orchards, vineyard, plantation, grasslands, lawns or forests, or waterways, canals or other non-cultivated lands.

When the compound (I) of the present invention is used as an active ingredient of herbicides, it is usually formulated with solid or liquid carriers or diluents as well as surfactants and other auxiliary agents into conventional formulations such as emulsifiable concentrates, wettable powders, flowables, granules, concentrated emulsion, water-dispersible granules and solutions.

These formulations contain the compound (I) of the present invention as an active ingredient at a content within the range of 0.003% to 80% by weight, preferably 0.01% to 70% by weight, based on the total weight of each of the formulations.

Examples of the solid carder ok diluent are fine powders or granules of mineral matters such as kaolin clay, attapulgite clay, bentonite, terra alba, pyrophyllite, talc, diatomaceous earth and calcite; organic substances such as walnut shell powder; water-soluble organic substances such as urea; inorganic salts such as ammonium sulfate; and synthetic hydrous silica. As the liquid carrier or diluent, there can be exemplified aromatic hydrocarbons such as alkylbenzenes (e.g., xylene), methylnaphthalene and phenylxylylethane; alcohols such as isopropanol, ethylene glycol and 2-ethoxyethanol; esters such as phthalic acid dialkyl esters; ketones such as acetone, cyclohexanone and isophorone; mineral oils such as machine oil; vegetable oils such as soybean oil and cotton seed oil; dimethylsulfoxide, N,N-dimethylformamide, acetonitrile, N-methylpyrrolidone, water and the like.

Examples of the surfactant used for emulsification, dispersing or spreading are those of anionic type, such as alkylsulfates, alkylsulfonates, alkylarylsulfonates, dialkylsulfosuccinates and phosphates of polyoxyethylene alkylaryl ether; and those of nonionic type, such as polyoxyethylene alkyl ethers, polyoxyethylene alkylaryl ethers, polyoxyethylene polyoxypropylene block copolymers, sorbitan fatty acid esters and polyoxyethylene sorbitan fatty acid esters.

Examples of the auxiliary agent used for formulation are ligninsulfonates, alginates, polyvinyl alcohol, gum arabic, carboxymethyl cellulose (CMC) and isopropyl acid phosphate (PAP).

The compound (I) of the present invention is usually formulated in any suitable formulation and used pre-emergence or post-emergence control of unfavorable weeds in upland fields and paddy fields. The soil treatment includes soil surface treatment and soil incorporation. The foliar treatment includes application over the plants and directed application to the weeds to keep any chemical off the crop foliage.

Further, the compound (I) of the present invention may be used together with other herbicide to enhance its herbicidal activity. Moreover, it may also be used in admixture with insecticides, acaricides, nematocides, fungicides, plant growth regulators, fertilizers, soil improver and the like.

When the compound (I) of the present invention is used as an active ingredient of herbicides, the dosage thereof is usually in the range of from 0.1 to 8000 grams, preferably from 1 to 2000 grams, per hectare, although it may vary depending upon the prevailing weather conditions, formulation type employed, application timing, type of application, soil involved, crop and weed species, and the like. A designated amount of the compound (I) formulated in the form of an emulsifiable concentrate, wettable powder, flowable, concentrated emulsion, water-dispersible granule, solution or the like, may usually be employed by diluting it with water at a volume of about 10 to 1000 liters per hectare, if necessary, with addition of an adjuvant such as a spreading agent. The compound (I) formulated in the form of a granule or some kinds of flowables or solutions may usually be applied without any dilution.

Examples of the adjuvant include, in addition to the surfactants as described above, polyoxyethylene resin acids (esters), ligninsulfonates, abietates, dinaphthyl methanedisulfonates, crop oil concentrates and crop oils such as soybean oil, corn oil, cotton seed oil and sunflower oil.

The compound (I) of the present invention can also be used as an active ingredient of harvesting aids such as defoliants and desiccating agents for cotton and desiccating agents for potato (*Solanum tuberosum*). In that case, the compound (I) is usually formulated in the same manner as the case where it is used as an active ingredient of herbicides, and used alone or in admixture with other harvesting aids.

The present invention will be further illustrated by way of the following production examples, formulation examples and test examples, which are not to be construed to limit the scope thereof. The compounds of the present invention are designated by the corresponding numbers as shown in Table 1.

Production Example 1: Preparation of Compound (1)

In 5 ml of xylene, 0.5 g of 1-[4-chloro-6-fluoro-3-hydroxy-2-(2-methyl-2-propenyl)phenyl]-3-methyl-4-trifluoromethyl-1,2,3,6-tetrahydropyrimidine-2,6-dione and 50 mg of p-toluenesulfonic acid monohydrate were dissolved, and the solution was refluxed for 5 hours. After completion of the reaction, the reaction solution was poured into water, and the mixture was extracted with 100 ml of diethyl ether. The extract was washed with water, dried and concentrated. The residue was purified by silica gel chromatography (eluent; hexane: ethyl acetate =2: 1), which afforded 0.1 g of compound (1).

$^1$H-NMR δ(ppm) [60 MHz, CDCl$_3$]: 1.55 (6H, s), 2.9–3.1 (2H, m), 3.61 (3H, s), 6.42 (1H, s), 7.18 (1H, d, J=10 Hz).

Production Example 2: Preparation of Compound (4)

In 5 ml of chloroform, 0.4 g of 1-[4-chloro-6-fluoro-3-hydroxy-2-(2-methyl-2-propenyl)phenyl]-3-methyl-4-trifluoromethyl- 1,2,3,6-tetrahydropyrimidine-2,6-dione was dissolved, to which a suspension containing 0.26 g of m-chloroperbenzoic acid in 5 ml of chloroform was added dropwise at room temperature, and the reaction was effected under reflux conditions for 3 hours. After completion of the reaction, the reaction mixture was cooled to room temperature, to which a saturated aqueous solution of sodium thiosulfate was added, and the mixture was stirred and extracted with chloroform. The extract was washed with an aqueous solution of sodium hydrogencarbonate, dried and concentrated. The residue was purified by silica gel chromatography (eluent; hexane :ethyl acetate=2: 1), which afforded 0.17 g of compound (4).

$^1$H-NMR δ(ppm) [60 MHz, CDCl$_3$]: 1.47 (3H, s), 2.3–2.6 (1H, br), 2.8–3.3 (2H, m), 3.56 (3H, s), 3.64 (2H, s), 6.39 (1H, s), 7.11 (1H, d, J=10 Hz).

Production Example 3: Preparation of Compound (11)

In 5 ml of pyridine, 0.5 g of compound (4) was dissolved, to which 50 mg of 4-dimethylaminopyridine was added. While ice cooling, 0.2 g of acetic anhydride was added, and the reaction was effected at room temperature for 3 hours. After completion of the reaction, the reaction mixture was extracted with diethyl ether. The extract was washed with diluted hydrochloric acid, dried and concentrated. The residue was purified by silica gel chromatography (eluent; hexane: ethyl acetate=2: 1), which afforded 0.2 g of compound ( 11).

$^1$H-NMR δ(ppm) [60 MHz, CDCl$_3$]: 1.29 (3H, s), 1.89 (3H, s), 2.7–2.9 (2H, m), 3.33 (3H, s), 4.00 (2H, s), 6.12 (1H, s), 6.88 (1H, d, J=10 Hz).

Production Example 4: Preparation of Compound (15)

In the same manner as described in Production Example 3, except that 0.17 g of propionic anhydride was used in place of acetic anhydride, 0.19 g of compound (15) was obtained.

$^1$H-NMR δ(ppm) [60 MHz, CDCl$_3$]: 1.03 (3H, t, J=8 Hz), 1.51 (3H, s), 2.30 (2H, q, J=8 Hz), 2.9–3.1 (2H, m), 3.52 (3H, s), 4.19 (2H, s), 6.30 (1 1H, s), 7.03 (1H, d, J=10 Hz).

Production Example 5: Preparation of Compound (23)

In 5 ml of acetone, 0.5 g of compound (4) was dissolved, to which 2 ml of Jones reagent was slowly added dropwise while ice cooling, followed by stirring for 4 hours. After completion of the reaction, the reaction mixture was poured into water, and the mixture was extracted with ethyl acetate. The extract was washed with water, dried and concentrated, which afforded 0.45 g of compound (23).

$^1$H-NMR δ(ppm) [60 MHz, CDCl$_3$]: 1.75 (3H, s), 2.9–3.3 (2H, m), 3.53 (3H, s), 6.29 (1H, s), 7.05 (1H, d, J=10 Hz).

Production Example 6: Preparation of Compound (24)

In 5 ml of methanol, 0.45 g of compound (23) was dissolved, to which 50 mg of p-toluenesulfonic acid monohydrate was added, and the reaction was effected under reflux conditions for 3 hours. After completion of the reaction, the reaction mixture was extracted with diethyl ether. The extract was washed with water, dried and concentrated. The residue was purified by silica gel chromatography (eluent; hexane: ethyl acetate=4: 1), which afforded 0.18 g of compound (24).

$^1$H-NMR δ(ppm) [60 MHz, CDCl$_3$]: 1.74 (3H, s), 3.1–3.5 (2H, m), 3.53 (3H, s), 3.76 (3H, s), 6.27 (1H, s), 7.03 (1H, d, J=10 Hz).

Production Example 7: Preparation of Compound (25)

In the same manner as described in Production Example 6, except that 0.5 g of compound (23) and 5 ml of ethanol were used, 0.26 g of compound (25) was obtained.

$^1$H-NMR δ(ppm) [60 MHz, CDCl$_3$]: 1.24 (3H, t, J=7 Hz), 1.70 (3H, s), 3.1–3.5 (2H, m), 3.52 (3H, s), 4.22 (2H, q, J=7 Hz), 6.31 (1H, s), 7.09 (1H, d, J=10 Hz).

Production Example 8: Preparation of Compound (32)

In the same manner as described in Production Example 6, except that 0.5 g of compound (23) and 5 ml of 1-butanol were used, 0.13 g of compound (32) was obtained.

$^1$H-NMR δ(ppm) [60 MHz, CDCl$_3$]: 0.91 (3H, t, J=6 Hz), 1.1–1.9 (4H, m), 1.73 (3H, s), 3.1–3.5 (2H, m), 3.55 (3H, s), 4.17 (2H, t, J=6 Hz), 6.31 (1H, s), 7.08 (H, d, J=10 Hz).

Production Example 9: Preparation of Compound (38)

In the same manner as described in Production Example 6, except that 0.5 g of compound (23) and 1 ml of propargyl alcohol were used, 0.16 g of compound (38) was obtained.

$^1$H-NMR δ(ppm) [60 MHz, CDCl$_3$]: 1.74 (3H, s), 2.49 (1H, t, J=2 Hz), 3.1–3.5 (2H, m), 3.50 (3H, s), 4.71 (2H, d, J=2 Hz), 6.26 (1H, s), 7.04 (1H, d, J=10 Hz).

Production Example 10: Preparation of Compound (39)

In the same manner as described in Production Example 3, except that 0.5 g of compound (4) and 0.17 g of benzoyl chloride were used, 0.18 g of compound (39) was obtained.

m.p., 157°–158° C.;

$^1$H-NMR δ(ppm) [60 MHz, CDCl$_3$]: 1.64 (3H, s), 3.1–3.3 (2H, m), 3.54 (3H, s), 4.3–4.5 (2H, m), 6.35 (1H, s), 7.10 (1H, d, J=10 Hz), 7.4–7.7 (3H, m), 7.8–8.1 (2H, m).

Production Example 11: Preparation of Compound (49)

In chloroform, 6.0 g of 1-[4-chloro-3-hydroxy-2-(2-methyl-2-propenyl)-phenyl]-3-methyl-4-trifluoromethyl- 1,2,3,6-tetrahydropyrimidine-2,6-dione was dissolved, to which 7.1 g of m-chloroperbenzoic acid was added, and the mixture was refluxed for 2 hours. After completion of the reaction, the reaction mixture was cooled to room temperature, to which an aqueous solution of sodium hydrogensulfite was added, and the mixture was extracted with chloroform. The organic layer was washed with aqueous solution potassium carbonate and water, dried and concentrated, which afforded 5.6 g of compound (49).

$^1$H-NMR δ(ppm) [60 MHz, CDCl$_3$]: 1.48 (3H, s), 2.05–2.49 (1H, br), 2.87 (1H, s, br), 3.06 (1H, s, br), 3.54 (3H, s), 3.64 (2H, s, br), 6.29 (1H, (1H, d, J=8 Hz), 7.22 (1H, s, J=8 Hz).

Production Example 12: Preparation of Compound (50)

In 8 ml of N,N-dimethylformamide, 0.3 g of compound (49) was dissolved, to which 0.5 ml of methyl iodide and 0.05 g of sodium hydride (60% in oil) were added at 5° C., and the mixture was warmed to room temperature and stirred for 6 hours. After completion of the reaction, the reaction mixture was poured into water, and the mixture was extracted with ethyl acetate. The extract was washed with water, dried and concentrated. The residue was purified by preparative thin layer chromatography, which afforded 0.12 g of compound (50).

$^1$H-NMR δ(ppm) [300 MHz, CDCl$_3$]: 1.52 (3×½H, s), 1.53 (3×½H, s), 2.78 (½H, d, J=16 Hz), 2.80 (½H, d, J=16 Hz), 3.10 (½H, d, J=16 Hz), 3.13 (½H, d, J=16 Hz), 3.40 (3×½H, s), 3.41 (3×½H, s), 3.49 (2H, m), 3.55 (3H, s), 3.64 (2H, s, br), 6.29 (1H, s), 6.59 (1H, d, J=8 Hz), 7.22 (1H, s, J=8 Hz).

Production Example 13: Preparation of Compound (53)

In 10 ml of chloroform, 0.3 g of compound (49) was dissolved, to which 0.5 ml of diisopropylethylamine and 0.15 g of chloromethyl methyl ether were added, and the mixture was stirred at room temperature for 17 hours. After completion of the reaction, the reaction mixture was poured into water, and the mixture was extracted with ethyl acetate. The organic layer was dried and concentrated. The residue was purified by preparative thin layer chromatography, which afforded 0.23 g of compound (53).

$^1$H-NMR δ(ppm) [300 MHz, CDCl$_3$]: 1.54 (3H, s), 2.82 (½H, d, J=16 Hz), 2.83 (½H, d, J=16 Hz), 3.15 (½H, d, J=16 Hz), 3.16 (½H, d, J=16 Hz), 3.347 (3×½H, s), 3.355 (3×½H, s), 3.55 (3H, s), 3.63 (2H, m), 4.65 (2H, m), 6.34 (1H, s), 6.64 (1H, d, J=8.5 Hz), 7.24 (1H, d, J=8.5 Hz).

Production Example 14: Preparation of Compound (56)

To 0.2 g of compound (49), 1.5 ml of pyridine and 1.5 ml of acetic anhydride were added, and the mixture was stirred at room temperature for 15 hours. After completion of the reaction, the reaction mixture was concentrated. The residue was purified by preparative thin layer chromatography, which afforded 0.18 g of compound (56).

$^1$H-NMR δ(ppm) [250 MHz, CDCl$_3$]: 1.58 (3H, s), 2.07 (3H, s), 2.92 (½H, d, J=16 Hz), 2.93 (½H, d, J=16 Hz), 3.12 (1H, d, J=16 Hz), 3.59 (3H, s), 4.22 (1H, d, J=12 Hz), 4.30 (½H, d, J=12 Hz), 4.31 (½H, d, J=12

Hz), 6.38 (1H, s), 6.69 (1H, d, J=8.5 Hz), 7.30 (1H, d, J=8.5 Hz).

Production Example 15: Preparation of Compound (69)

In 40 ml of acetone, 3.0 g of compound (49) was dissolved, to which Jones reagent was added at room temperature until the starting material disappeared. After completion of the reaction, 2-propanol was added to the reaction mixture, which was stirred for 1 hour. The reaction mixture was poured into water, and the mixture was extracted with diethyl ether. The organic layer was washed with water, dried and concentrated, which afforded 2.72 g of compound (69).

$^1$H-NMR δ(ppm) [60 MHz, CDCl$_3$]: 1.70 (3H, s), 3.11 (1H, s, br), 3.38 (1H, s, br), 3.49 (3H, s, br), 6.26 (1H, s), 6.61 (1H, d, J=8 Hz), 7.19 (1H, d, J=8 Hz).

Production Example 16: Preparation of Compound (70)

In 30 ml of methanol, 0.5 g of compound (69) was dissolved, to which 0.1 ml of sulfuric acid was added, and the mixture was refluxed for 3 hours. After completion of the reaction, the reaction mixture was poured into water, and the mixture was extracted with diethyl ether. The extract was washed with water, dried and concentrated. The residue was purified by preparative thin layer chromatography, which afforded 0.24 g of compound (70).

$^1$H-NMR δ(ppm) [60 MHz, CDCl$_3$]: 1.74 (3H, s), 3.15 (1H, s, br), 3.42 (1H, s, br), 3.52 (3H, s), 3.77 (3H, s), 6.29 (1H, s), 6.64 (1H, d, J=8 Hz) 7.23 (1H, d, J=8 Hz).

Production Example 17: Preparation of Compound (72)

In the same manner as described in Production Example 16, except that 30 ml of 1-propanol was used in place of methanol, 0.3 g of compound (72) was obtained.

$^1$H-NMR δ(ppm) [60 MHz, CDCl$_3$]: 0.90 (3H, t, J=7 Hz), 1.39-1.85 (2H, m), 1.74 (3H, s), 3.16 (1H, s), 3.41 (1H, s), 3.52 (3H, s), 4.11 (2H, t, J=7 Hz), 6.31 (1H, s), 6.64 (1H, d, J=8 Hz), 7.24 (1H, d, J=8 Hz).

Production Example 18: Preparation of Compound (73)

In the same manner as described in Production Example 16, except that 30 ml of 1-butanol was used in place of methanol, 0.2 g of compound (73) was obtained.

$^1$H-NMR δ(ppm) [60 MHz, CDCl$_3$]: 0.90 (3H, t, J=7 Hz), 1.12-1.92 (4H, m), 1.72 (3H, s), 3.14 (1H, s), 3.40 (1H, s), 3.51 (3H, s), 4.14 (2H, t, J=7 Hz), 6.29 (1H, s), 6.63 (1H, d, J=8 Hz), 7.72 (1H, d, J=8 Hz).

Production Example 19: Preparation of Compound (75)

In the same manner as described in Production Example 16, except that 30 ml of 2-propanol was used in place of methanol, 0.3 g of compound (75) was obtained.

$^1$H-NMR δ(ppm) [60 MHz, CDCl$_3$]: 1.37 (6H, d, J=7 Hz), 1.73 (3H, s), 3.14 (3H, s), 3.39 (1H, s), 3.52 (1H, s), 5.02 (1H, hp, J=7 Hz), 6.31 (1H, s,) 6.63 (1H, d, J=8 Hz), 7.24 (1H, d, J=8 Hz).

Production Example 20: Preparation of 1-[4-chloro-6-fluoro-3-hydroxy-2-(2-methyl-2-propenyl)phenyl]-3-methyl-4-trifluoromethyl-1,2,3,6,-tetrahydropyrimidine-2,6-dione In 50 ml of N,N-diethylaniline, 21.6 g of 1-[4-chloro-2-fluoro-5-(2-methyl-2-propenyloxy)phenyl]-3-methyl-4-trifluoromethyl-1,2,3,6-tetrahydropyrimidine-2,6,-dione was dissolved, and the solution was refluxed for 4 hours. After completion of the reaction, the reaction mixture was cooled to room temperature and extracted with diethyl ether. The extract was washed with diluted hydrochloric acid, dried and concentrated. The residue was purified by silica gel chromatography (eluent; hexane: ethyl acetate=2:1 ), which afforded 19.5 g of the desired compound.

$^1$H-NMR δ(ppm) [60 MHz, CDCl$_3$]: 1.60 (3H, s), 3.28 (2H, s), 3.48 (3H, s), 4.4-4.6 (1H, m), 4.6-4.8 (1H, m), 5.76 (1H, s), 6.36 (1H, s), 7.09 (1H, d, J=10 Hz).

Production Example 21: Preparation of 1-[4-chloro-3-hydroxy-2-(2-methyl-2-propenyl)phenyl]-3-methyl-4-trifluoromethyl-1,2,3,6,-tetrahydropyrimidine-2,6-dione In 150 ml of N,N-dimethylaniline, 7.4 g of 1-[4-chloro-3-(2-methyl-2-propenyloxy)phenyl]-3-methyl-4-trifluoromethyl- 1,2,3,6,-tetrahydropyrimidine-2,6-dione was dissolved, and the solution was stirred at 160° C. for 3 hours. After completion of the reaction, the reaction mixture was cooled to room temperature and poured into water. The mixture was extracted with diethyl ether. The organic layer was washed with dilute hydrochloric acid, dried and concentrated, which afforded 6.2 g of the desired compound.

$^1$H-NMR δ(ppm) [60 MHz, CDCl$_3$]: 1.58 (3H, s), 3.28 (2H, s), 3.46 (3H, s), 4.45 (1H, s), 4.58 (1H, s), 6.14 (1H, s), 6.26 (1H, s), 6.60 (1H, d, J=8 Hz), 7.26 (1H, d, J=8 Hz).

The following will describe a production example of compound (IV).

Production Example 22

In 500 ml of chloroform, 50 g of 1-[4-chloro-6-fluoro-3-hydroxy-2-(2-methyl-2-propenyl)phenyl]-3-methyl-4-trifluoromethyl-1,2,3,6-tetrahydropyrimidine-2,6-dione was dissolved, to which 30.0 g of m-chloroperbenzoic acid was added, and the reaction was effected at 60° C. for 4.5 hours. After completion of the reaction, the reaction mixture was cooled to room temperature and subjected to fractionation with a separatory funnel using chloroform and an aqueous solution of sodium sulfite. The organic layer was washed with a saturated aqueous solution of sodium hydrogencarbonate and then water, dried and concentrated. The residue was subjected to recrystallization, which afforded 46 g of 1-[4-chloro-6-fluoro-3-hydroxy-2-(2,3-epoxy-2-methylpropyl)phenyl]-3-methyl-4-trifluoromethyl-1,2,3,6-tetrahydropyrimidine-2,6-dione.

$^1$H-NMR δ(ppm) [60 MHz, CDCl$_3$]1.29 ($\frac{1}{2}$×3H, s), 1.31 ($\frac{1}{2}$×3H, s,), 2.75 (3H, m), 3.10 (1H, m), 3.58 (3H, s), 6.31 (1H, s), 7.20 (1H, d, J=8 Hz), 7.45 (1H, s).

The following will describe formulation examples wherein parts are by weight. The compounds of the present invention are designated by the corresponding numbers as shown in Table 1.

Formulation Example 1

Fifty parts of any one of the compounds (1), (4), (11), (13)–(17), (23)–(25), (28), (29), (32), (33), (36), (38), (39), (44), (49), (50), (53), (56), (70), (72), (73) and (75), 3 parts of calcium ligninsulfonate, 2 parts of sodium laurylsulfate and 45 parts of synthetic hydrous silicate are well mixed while being powdered to obtain a wettable powder.

Formulation Example 2

Ten parts of any one of the compounds ( 1 ), (4), ( 11 ), ( 13 )–(17), (23)–(25), (28), (29), (32), (33), (36), (38), (39), (44), (49), (50), (53), (56), (70), (72), (73) and (75), 14 parts of polyoxyethylene styryl phenyl ether, 6 parts of calcium dodecylbenzene-sulfonate, 35 parts of xylene and 35 parts of cyclohexanone are well mixed to obtain an emulsifiable concentrate.

Formulation Example 3

Two parts of any one of the compounds (1), (4), (11), (13)–(17), (23)–(25), (28), (29), (32), (33), (36), (38), (39), (44), (49), (50), (53), (56), (70), (72), (73) and (75), 2 parts of synthetic hydrous silicate, 2 parts of calcium ligninsulfonate, 30 parts of bentonite and 64 parts of kaoline clay are well mixed while being powdered. The mixture is then kneaded with water, granulated and dried to obtain granules.

Formulation Example 4

Twenty five parts of any one of the compounds (1), (4), (1 I), (13), (14), (16), (17), (23), (24), (25), (28), (29), (32), (33), (38), (39), (49) and (70), 50 parts of 10% solution of polyvinylalcohol and 25 parts of water are well mixed, and the mixture was then pulverized until the particle size thereof becomes not greater than 5 microns to obtain a flowable.

The following will describe test examples. The compounds of the present invention are designated by the corresponding numbers as shown in Table 1, and the compounds used for comparison are designated by the numbers as shown in Table 2.

TABLE 2

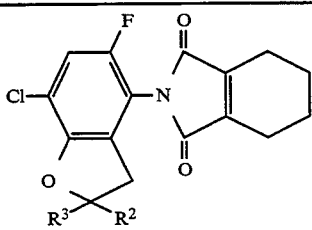

| Compound No. | $R^2$ | $R^3$ | Remarks |
|---|---|---|---|
| A | $CH_3$ | $CH_3$ | U.S. Pat. No. 4,881,967 |
| B | $CH_3$ | $CH_2OH$ | " |
| C | $CH_3$ | $CH_2OCOCH_3$ | " |

The herbicidal activity on weeds and the phytotoxicity to crop plants were determined by visual observation as to the degree of germination and growth of the test plants (i.e., weeds and crop plants), and rated with an index 0, 1, 2, 3, 4 or 5, the numeral "0" indicating little or no difference as seen in comparison with the untreated plants and the numeral "5" indicating the complete death of the test plants or the complete inhibition of their germination or growth.

Test Example 1

Cylindrical plastic pots (diameter, 10 cm; height, 10 cm) were filled with upland field soil, and the seeds of wild oat and tall morningglory were sowed therein and covered with soil. The test compound formulated in the emulsifiable concentrate according to Formulation Example 2 was diluted with water, and the dilution was sprayed onto the soil surface by an automatic sprayer at an application amount of 1000 liters per hectare. The test plants were grown in a greenhouse for 19 days, and the herbicidal activity was examined. The results are shown in Table 3.

TABLE 3

| Compound No. | Dosage (a.i. g/ha) | Herbicidal activity Wild oat | Tall morningglory |
|---|---|---|---|
| (1) | 31 | 5 | 5 |
| (4) | 31 | 5 | 5 |
| (11) | 31 | 5 | 5 |
| (13) | 31 | 5 | 5 |
| (14) | 31 | 5 | 5 |
| (15) | 31 | 5 | 5 |
| (16) | 31 | 5 | 4 |
| (17) | 31 | 5 | 5 |
| (29) | 31 | 4 | 4 |
| A | 31 | 1 | 1 |
| B | 31 | 3 | 2 |
| C | 31 | 3 | 1 |

Test Example 2

Cylindrical plastic pots (diameter, 10 cm; height, 10 cm) were filled with upland field soil, and seeds of wild oat were sowed therein and cultivated in a greenhouse for 7 days. After that, the test compound formulated in the emulsifiable concentrate according to Formulation Example 2 was diluted with water containing a spreading agent, and the dilution was sprayed over the foliage of the test plants by an automatic sprayer at an application amount of 1000 liters per hectare. After the treatment, the test plants were further grown in the greenhouse for 19 days, and the herbicidal activity was examined. The results are shown in Table 4.

TABLE 4

| Compound No. | Dosage (a.i. g/ha) | Herbicidal activity Wild oat |
|---|---|---|
| (1) | 31 | 5 |
| (11) | 31 | 4 |
| (13) | 31 | 4 |
| (15) | 31 | 4 |
| (16) | 31 | 5 |
| (23) | 31 | 5 |
| (24) | 31 | 5 |
| (25) | 31 | 4 |
| (28) | 31 | 5 |
| (29) | 31 | 5 |
| (32) | 31 | 5 |
| (33) | 31 | 5 |
| (36) | 31 | 5 |
| (38) | 31 | 5 |
| A | 31 | 2 |
| C | 31 | 2 |

Test Example 3

Plastic pots (25 cm×18 cm×7 cm) were filled with upland field soil, and the seeds of soybean, tall morningglory, barnyardgrass and Johnsongrass were sowed therein and covered with soil. The test compound formulated in an emulsifiable concentrate according to Formulation Example 2 was diluted with water, and the dilution was sprayed onto the soil surface by an automatic sprayer at an application amount of 1000 liters per hectare. The test plants were grown in a greenhouse for 18 days, and the herbicidal activity and the phytotoxicity were examined. The results are shown in Table 5.

TABLE 5

| Compound No. | Dosage (a.i. g/ha) | Phytotoxicity Soybean | Herbicidal activity Tall morningglory | Barnyardgrass | Johnsongrass |
|---|---|---|---|---|---|
| (23) | 31 | 0 | 5 | 4 | 4 |
| (28) | 125 | 1 | 5 | 5 | 5 |
| | 31 | 0 | 5 | 5 | 5 |

TABLE 5-continued

| Compound No. | Dosage (a.i. g/ha) | Phytotoxicity Soybean | Herbicidal activity | | |
|---|---|---|---|---|---|
| | | | Tall morningglory | Barnyardgrass | Johnsongrass |
| (29) | 125 | 1 | 4 | 5 | 5 |
| (32) | 31 | 0 | 4 | 5 | 4 |
| (53) | 63 | 1 | 4 | 5 | 5 |
| (70) | 125 | 1 | 5 | 5 | 4 |
| A | 125 | 1 | 3 | 3 | 4 |
| | 31 | 0 | 1 | 1 | 2 |

Test Example 4

Plastic pots (25cm×18 cm×7 cm) were filled with upland field soil, and the seeds of wheat, catchweed bedstraw, birdseye speedwell and field pansy were sowed therein, and cultivated in a greenhouse for 29 days. The test compound formulated in the emulsifiable concentrate according to Formulation Example 2 was diluted with water, and the dilution was sprayed over the foliage of the test plants by an automatic sprayer at an application amount of 1000 liters per hectare. The test plants were further grown in the greenhouse for 25 days, and the herbicidal activity and crop phytotoxicity were examined. At the time of the application, the test plants were generally at 1 to 4 leaf stage and in 3-25 cm height, although the growing stage of the test plants varied depending on their species. The results are shown in Table 6.

TABLE 6

| Compound No. | Dosage (a.i. g/ha) | Phytotoxicity Wheat | Herbicidal activity | | |
|---|---|---|---|---|---|
| | | | Catchweed bedstraw | Birdseye speedwell | Field pansy |
| (1) | 16 | 1 | 5 | 5 | 5 |
| (4) | 16 | 1 | 5 | 5 | 5 |
| (11) | 16 | 0 | 5 | 5 | 5 |
| (14) | 16 | 1 | 4 | 4 | 5 |
| (15) | 16 | 1 | 5 | 5 | 5 |
| (16) | 16 | 1 | 4 | 4 | 5 |
| (17) | 16 | 1 | 4 | 5 | 5 |
| (23) | 16 | 1 | 4 | 5 | 5 |
| (24) | 4 | 1 | 5 | 5 | 5 |
| (25) | 16 | 0 | 5 | 5 | 5 |
| | 4 | 0 | 4 | 5 | 4 |
| (28) | 16 | 1 | 5 | 5 | 5 |
| (29) | 16 | 1 | 5 | 5 | 5 |
| (32) | 16 | 1 | 5 | 5 | 5 |
| | 4 | 1 | 5 | 4 | 5 |
| (33) | 16 | 1 | 5 | 5 | 5 |
| (36) | 16 | 1 | 4 | 5 | 5 |
| (38) | 16 | 1 | 4 | 5 | 5 |
| | 4 | 1 | 4 | 5 | 5 |
| (70) | 16 | 0 | 5 | 5 | 5 |
| A | 31 | 1 | 3 | 4 | 4 |
| | 8 | 1 | 3 | 3 | 3 |
| B | 31 | 2 | 3 | 3 | 5 |
| | 8 | 1 | 3 | 1 | 3 |
| C | 31 | 2 | 4 | 3 | 4 |
| | 8 | 1 | 3 | 1 | 3 |

Test Example 5

Plastic pots (19 cm×29 cm×8 cm) were filled with upland field soil, and the seeds of cotton were sowed therein, and cultivated in a greenhouse for 3 months. The test compound formulated in the emulsifiable concentrate according to Formulation Example 2 was diluted with water containing a spreading agent, and the dilution was sprayed over the foliage of the test plant by a spray machine at an application amount of 1000 liters per hectare. After the treatment, the test plants were further gown in the greenhouse for 9 days, and the desiccating effect of the foliage of the cotton plants was examined. At the time of the application, the test plants were in 50 cm height and began to set bolls. The desiccating effect on cotton foliage was determined by 0–100 (%), the numeral "0" indicating no difference in comparison with untreated plant and the numeral "100" indicating the complete desiccating effect. The result is shown in Table 7.

TABLE 7

| Compound No. | Dosage (a.i. g/ha) | Desiccating effect (%) |
|---|---|---|
| (24) | 100 | 93 |

As described above, the compounds (I) of the present invention have excellent herbicidal activity against various unfavorable weeds under the soil treatment or foliar treatment on upland fields and under the flooding treatment on paddy fields, and some of them exhibit excellent selectivity between crops and weeds; therefore, they are useful as active ingredients of herbicides.

What is claimed is that:

1. A compound of the formula:

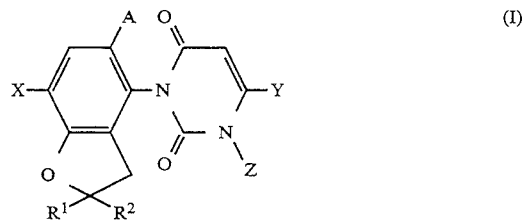

wherein A is hydrogen, fluorine or chlorine; X is hydrogen, fluorine, chlorine or bromine; Y is methyl optionally substituted with one or more halogen atoms; Z is methyl or amino; $R^1$ is $C_1$-$C_6$ alkyl; and $R^2$ is $C_1$-$C_6$ alkyl, $C_1$-$C_6$ haloalkyl, $C_1$-$C_6$ hydroxyalkyl, $C_1$-$C_6$ alkoxy($C_1$-$C_6$)alkyl, $C_1$-$C_6$ alkoxy($C_1$-$C_6$)alkoxyl ($C_1$-$C_6$)-alkyl, $C_1$-$C_7$ acyloxy($C_1$-$C_6$)alkyl, carboxyl, $C_1$-$C_6$ alkoxycarbonyl, $C_1$-$C_6$ haloalkoxycarbonyl, $C_3$-$C_6$ cycloalkoxycarbonyl, $C_2$-$C_6$ alkynyloxycarbonyl, aminocarbonyl, $C_1$-$C_6$ alkylaminocarbonyl or phenylaminocarbonyl having a phenyl group optionally substituted with $C_1$-$C_6$ alkyl, $C_1$-$C_6$ alkoxy, $C_1$-$C_6$ haloalkyl, $C_1$-$C_6$ haloalkoxy, halogen, nitro, cyano or $C_1$-$C_6$ alkylthio.

2. The compound according to claim 1, wherein $R^1$ is $C_1$-$C_3$ alkyl.

3. The compound according to claim 1, wherein $R^1$ is methyl.

4. The compound according to claim 1, wherein A is hydrogen.

5. The compound according to claim 1, wherein $R^2$ is $C_1$-$C_3$ alkyl, $C_1$-$C_3$ haloalkyl, $C_1$-$C_3$ hydroxyalkyl, $C_1$-$C_3$ alkoxy($C_1$-$C_3$)alkyl, $C_1$-$C_3$ alkoxy($C_1$-$C_3$)alkoxy($C_1$-$C_3$)alkyl, $C_1$-$C_7$ acyloxy($C_1$-$C_3$)alkyl, carboxyl, $C_1$-$C_6$ alkoxycarbonyl, $C_1$-$C_6$ haloalkoxycarbonyl, $C_3$-$C_6$ cycloalkoxycarbonyl or $C_2$-$C_4$ alkynyloxycarbonyl.

6. The compound according to claim 1, wherein $R^2$ is methyl, ethyl, fluoromethyl, chloromethyl, bromomethyl, fluoroethyl, chloroethyl, bromoethyl, hydroxymethyl, hydroxyethyl, methoxymethyl, ethoxymethyl, isopropyloxymethyl, methoxy methoxymethyl, ethoxymethoxymethyl, $C_1$-$C_7$ acyloxymethyl, $C_1$-$C_7$ acyloxyethyl, carboxyl, methoxycarbonyl, ethoxycarbonyl, n-propyloxycarbonyl, i-propyloxycarbonyl, n-butyloxycarbonyl, i-butyloxycarbonyl, t-butyloxycarbonyl, n-pentyloxycarbonyl, i-pentyloxycarbonyl, t-pentyloxycarbonyl, $C_1$-$C_3$ haloalkoxycarbonyl, cyclopentyloxycarbonyl or cyclohexyloxycarbonyl.

7. The compound according to claim 1, wherein Z is amino.

8. The compound according to claim 5, wherein $R^1$ is $C_1$-$C_3$ alkyl.

9. The compound according to claim 5, wherein $R^1$ is methyl.

10. The compound according to claim 6, wherein $R^1$ is $C_1$-$C_3$ alkyl.

11. The compound according to claim 6, wherein $R^1$ is methyl.

12. The compound according to claim 6, wherein A is fluorine, X is chlorine, Y is trifluoromethyl, Z is methyl, and $R^1$ is $C_1$-$C_3$ alkyl.

13. The compound according to claim 6, wherein A is fluorine, X is chlorine, Y is trifluoromethyl, Z is methyl, and $R^1$ is methyl.

14. The compound according to claim 6, wherein A is hydrogen, X is chlorine, Y is trifluoromethyl, Z is methyl, and $R^1$ is $C_1$-$C_3$ alkyl.

15. The compound according to claim 6, wherein A is hydrogen, X is chlorine, Y is trifluoromethyl, Z is methyl, and $R^1$ is methyl.

16. A herbicidal composition comprising, as an active ingredient, a herbicidally effective amount of the compound according to claim 1, and an inert carrier or diluent.

17. A method for exterminating unfavorable weeds, which comprises applying a herbicidally effective amount of the compound according to claim 1 to an area where the unfavorable weeds grow or will grow.

18. A compound of the formula:

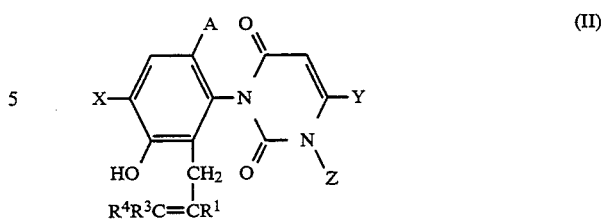

(II)

wherein A is hydrogen, fluorine or chlorine; X is hydrogen, fluorine, chlorine or bromine; Y is methyl optionally substituted with one or more halogen atoms; Z is methyl or amino; $R^1$ is $C_1$-$C_6$ alkyl; and $R^3$ and $R^4$ are the same or different and are hydrogen or $C_1$-$C_6$ alkyl with the proviso that the total number of carbon atoms in the $R^3$ and $R^4$ is not greater than 6.

19. A compound of the formula:

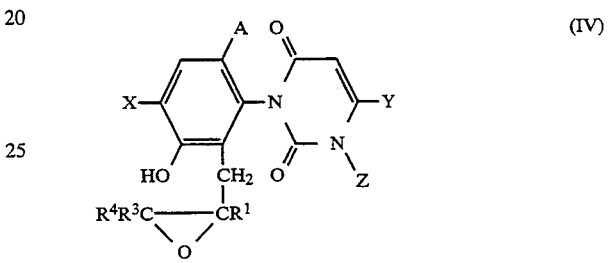

(IV)

wherein A is hydrogen, fluorine or chlorine; X is hydrogen, fluorine, chlorine or bromine; Y is methyl optionally substituted with one or more halogen atoms; Z is methyl or amino; $R^1$ is $C_1$-$C_6$ alkyl; and $R^3$ and $R^4$ are the same or different and are hydrogen or $C_1$-$C_6$ alkyl with the proviso that the total number of carbon atoms in the $R^3$ and $R^4$ is not greater than 6.

20. A compound according to claim 1, wherein Z is methyl.

* * * * *